(12) United States Patent
Gorman et al.

(10) Patent No.: US 6,465,638 B2
(45) Date of Patent: *Oct. 15, 2002

(54) **MULTIPLEXED PCR ASSAY FOR DETECTING DISSEMINATED *MYCOBACTERIUM AVIUM* COMPLEX INFECTION**

(75) Inventors: Kevin M. Gorman, Rochester, NY (US); John A. McElver, Des Moines, IA (US); Charles P. Cartwright, Plymouth, MN (US); David R. Patterson, Penfield, NY (US)

(73) Assignee: Ortho-Clinical Diagnostics, Inc., Rochester, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/102,831

(22) Filed: Jun. 23, 1998

(65) Prior Publication Data

US 2001/0019822 A1 Sep. 6, 2001

Related U.S. Application Data

(60) Provisional application No. 60/050,760, filed on Jun. 25, 1997.

(51) Int. Cl.$^7$ ............................................. C07H 21/04
(52) U.S. Cl. .................. 536/24.32; 536/24.3; 536/23.1; 435/6; 435/91.2
(58) Field of Search .................... 536/24.32, 24.3, 536/23.1; 435/6, 91.2

(56) References Cited

U.S. PATENT DOCUMENTS 5,574,145 A    11/1996   Barry et al.

FOREIGN PATENT DOCUMENTS

| EP | 0 272 009 B1 | 6/1988 |
| EP | 0 395 292 B1 | 10/1990 |
| EP | 0 612 356 B1 | 8/1991 |
| EP | 0 651 057 A1 | 3/1994 |
| EP | 0 525 095 B1 | 9/1995 |
| WO | 88/03957 | 11/1986 |
| WO | 95/06755 | 9/1993 |
| WO | 95/03412 | 2/1995 |
| WO | 96/00298 | 1/1996 |
| WO | 97/08340 | 7/1996 |

OTHER PUBLICATIONS

De Smet et al. Microbiology (1995) 141, 2739–2747.*
Booth et al. GenBank Accession No.: L12235. Apr. 26, 1993.*
Y. Abed, et al., "Identification and Stain Differeentiation of Mycobacterium Species on the Basis of DNA 16S–23S Spacer Region Polymorphism" Res. Microbiol 1995, 146, pp. 405–413.

Roger J. Booth et al., Homologs of *Mycobacterium leprae* 18–Kilodalton and *Mycobacterium tuberculosis* 19–Kilodalton Antigens in Other Mycfobacteria Infection and Immunity, Apr. 1993, pp. 1509–1515.
Richard Frothingham et al., "Sequence–Based Differentiation of Strains in the *Mycobacterium avium* Complex", Journal of Bacteriology, May 1993, pp. 2818–2825.
Richard Frothingham et al. "Molecular Phylogeny of the *Mycobacterium avium* Complex Demonstrates Clinically Meaningful Divisions", The Journal of Infectious Disease 1994, 169, pp. 305–312.
Jerzy K. Kulski et al., "Use of a Multiplex PCR To Detect and Identify *Mycobacterium avium* and *M. intracellulare* in Blood Culture Fluids of AIDS Patients", Journal of Clinical Microbiology, Mar. 1995, pp. 668–674, vol. 33, No. 3.
Jaygopal Nair et al., "Nucleotide Sequence Analysis and Serologic Characterization of the *Mycobacterium intracellulare* Homologue of the *Mycobacterium tuberculosis* 19 kDa Antigen", Molecular Microbiology (1992) 6 (11), pp. 1431–1439.
Lawrence G. Wayne et al., "Agents of Newly Recognized or Infrequently Encountered Mycobacterial Diseases" Clinical Microbiology Reviews, Jan. 1992, pp. 1–25.
Hajime Saito et al., "Identification of Various Serovar Strains of *Mycobacterium avium* Complex by Using DNA Probes Specific for *Mycobacterium avium* and *Mycobacterium intracellulare*" Journal of Clinical Microbiology, Aug. 1990, pp. 1694–1697 vol. 28, No. 8.
L. G. Wayne et al., "Serovar Determination and Molecular Taxonomic Correlation in *Mycobacterium avium*, *Mycobacterium intracellulare*, and *Mycobacterium scrofulaceum*: a Cooperative Study of the International Working Group on Mycobacterial Taxonomy", Int'l. Journal of Systematic Bacteriology, Jul. 1993, pp. 482–489, vol. 43, No. 3.
Mitchell A. Yakrus et al. "Geographic Distribution, Frequency, and Specimen Source of *Mycobacterium avium* complex Serotypes Isolated from Patients with Acquired Immunodeficiency Syndrome", Journal of Clinical Microbiology, May 1990, pp. 926–929 vol. 28, No. 5.
A.S. Mustafa et al., Establishment and Evaluation of a Mulitplex Polymerase Chain Reaction for Detection of Mycobacteria and Specific Identification of *Mycobacterium tuberculosis* Complex, Tubercle and Lung Disease (1995) 76, pp. 336–343.
1988 Catalog, pp. 39 & 40 Gene Characterization Kits. Stratagene.
Jaygopal Nair et al., "Nucleotide Sequence Analysis of the Ribosomal S12 Gene of *Mycobacterium intracellulare*", Nucleic Acids Research, 1993, vol. 21, No. 4 1039.

* cited by examiner

Primary Examiner—W. Gary Jones
Assistant Examiner—Juliet C. Einsmann
(74) Attorney, Agent, or Firm—Catherine K. Gowen

(57) ABSTRACT

The present invention relates to nucleic acid primers and probes specific for organisms of the *Mycobacterium avium* complex (MAC) and to their use in nucleic acid amplification methods for the detection and differentiation of such organisms in biological samples. The invention also relates to diagnostic kits for detecting and differentiating the various organisms comprising the MAC.

5 Claims, No Drawings

SEQUENCE LISTING

<160> NUMBER OF SEQ ID NOS: 16

<210> SEQ ID NO 1
<211> LENGTH: 25
<212> TYPE: DNA
<213> ORGANISM: Unknown
<220> FEATURE:
<223> OTHER INFORMATION: Description of Unknown Organism: Mycobacterium
      avium complex

<400> SEQUENCE: 1
ccctgagaca acactdggtc cgtcc                                              25

<210> SEQ ID NO 2

-continued

```
<211> LENGTH: 28
<212> TYPE: DNA
<213> ORGANISM: Mycobacterium avium

<400> SEQUENCE: 2
gtgcgcaaca gcaaatgatt gccagaca                                        28

<210> SEQ ID NO 3
<211> LENGTH: 28
<212> TYPE: DNA
<213> ORGANISM: Mycobacterium avium

<400> SEQUENCE: 3
tgcacaacag caaatgattg ccagacac                                        28

<210> SEQ ID NO 4
<211> LENGTH: 24
<212> TYPE: DNA
<213> ORGANISM: Mycobacterium avium

<400> SEQUENCE: 4
ccaccaagat ggagggactc caca                                            24

<210> SEQ ID NO 5
<211> LENGTH: 31
<212> TYPE: DNA
<213> ORGANISM: Mycobacterium avium

<400> SEQUENCE: 5
ccaatactca aacaccacac cccaccacca a                                    31

<210> SEQ ID NO 6
<211> LENGTH: 25
<212> TYPE: DNA
<213> ORGANISM: Unknown
<220> FEATURE:
<223> OTHER INFORMATION: Description of Unknown Organism: Mycobacterium
      avium complex

<400> SEQUENCE: 6
ccctgagaca acactgggtc cgtcc                                           25

<210> SEQ ID NO 7
<211> LENGTH: 25
<212> TYPE: DNA
<213> ORGANISM: Mycobacterium avium

<400> SEQUENCE: 7
ccctgagaca acactcggtc cgtcc                                           25

<210> SEQ ID NO 8
<211> LENGTH: 25
<212> TYPE: DNA
<213> ORGANISM: Unknown
<220> FEATURE:
<223> OTHER INFORMATION: Description of Unknown Organism: Mycobacterium
      avium complex

<400> SEQUENCE: 8
ccctgagaca acactcggtc ggtcc                                           25

<210> SEQ ID NO 9
<211> LENGTH: 25
<212> TYPE: DNA
<213> ORGANISM: Unknown
```

-continued

```
<220> FEATURE:
<223> OTHER INFORMATION: Description of Unknown Organism: Mycobacterium
      avium complex

<400> SEQUENCE: 9
gccctgagac aacactcggt cagtc                                          25

<210> SEQ ID NO 10
<211> LENGTH: 25
<212> TYPE: DNA
<213> ORGANISM: Mycobacterium intracellulare

<400> SEQUENCE: 10
ccctgagaca acactcggtc gatcc                                          25

<210> SEQ ID NO 11
<211> LENGTH: 24
<212> TYPE: DNA
<213> ORGANISM: Mycobacterium avium

<400> SEQUENCE: 11
cggctgttcg agtggcaaca agtc                                           24

<210> SEQ ID NO 12
<211> LENGTH: 23
<212> TYPE: DNA
<213> ORGANISM: Mycobacterium avium

<400> SEQUENCE: 12
ccgtcgatga tgaccttggt ccc                                            23

<210> SEQ ID NO 13
<211> LENGTH: 20
<212> TYPE: DNA
<213> ORGANISM: Mycobacterium avium

<400> SEQUENCE: 13
agtccgtcgg cgagcagcgg                                                20

<210> SEQ ID NO 14
<211> LENGTH: 25
<212> TYPE: DNA
<213> ORGANISM: Mycobacterium intracellulare

<400> SEQUENCE: 14
cgggacaagg tcgccaaggt caaga                                          25

<210> SEQ ID NO 15
<211> LENGTH: 23
<212> TYPE: DNA
<213> ORGANISM: Mycobacterium intracellulare

<400> SEQUENCE: 15
gggatgtagg ccgtcacctc aac                                            23

<210> SEQ ID NO 16
<211> LENGTH: 23
<212> TYPE: DNA
<213> ORGANISM: Mycobacterium intracellulare

<400> SEQUENCE: 16
gaccttccga agagcggagt tcg                                            23
```

MULTIPLEXED PCR ASSAY FOR DETECTING DISSEMINATED *MYCOBACTERIUM AVIUM* COMPLEX INFECTION

BACKGROUND OF THE INVENTION

This application claims the benefit of U.S. Provisional application Ser. No. 60/050,760, filed on Jun. 25, 1997.

FIELD OF THE INVENTION

The present invention relates to nucleic acid primers and probes specific for organisms of the *Mycobacterium avium* complex (MAC) and to their use in nucleic acid amplification methods for the detection and differentiation of such organisms in biological samples. The invention also relates to diagnostic kits for detecting and differentiating the various organisms comprising the MAC.

BACKGROUND INFORMATION

The *Mycobacterium avium* complex (MAC) is composed of a large number of organisms, many of which are classified as *M. avium* or *M. intracellulare*. In addition, there are a number of organisms within the MAC that cannot be properly classified because they have the characteristics of both *M. avium* and *M. intracellulare*, or because they have combined characteristics of another mycobacterium with either *M. avium* or *M. intracellulare* (Wayne, et al., International J. Systematic Bacteriol., 43(3):482–489 (1993)).

The *Mycobacterium avium* complex consists of at least 26 serovars. These organisms were originally defined by their agglutination in the presence of specific agglutinating antisera (through immune reaction with their cell wall surface antigens). *M. avium* is considered to include serovars 1 through 6, 8 through 11, and 21, while *M. intracellulare* is considered to include serovars 7, 12–17, 19, 20, 25 (Wayne, et al., Clin. Microbiol. Rev. 5:1–25 (1992) and H. Saito, et al., J. Clin. Microbiol., 28:1694–1697 (1990)).

Frothingham et al. (J. Bacteriol., 175(10):2818–2825 (1993)) further classified these organisms into sequevars. The sequevar classification was derived by sequencing the 16s–23s rRNA internal transcribed spacer region of reference strains of organisms representing the MAC. This classification system, based on the genetic sequence, revealed a wide range of genetic diversity among non-*M. avium*, non-*M. intracellulare* MAC strains. Frothingham et al. classified these reference strains as Mav-A through Mav-D, for *M. avium* organisms, Min-A, for *M. intracellulare* organisms, and MAC-A through MAC-H, for all *M. avium* complex strains that fit in neither of the avium or intracellulare categories (see also, Frothingham, et al., J. Infect. Diseases, 169:305–312 (1994)).

Infections caused by members of the MAC have become a major clinical problem, particularly in individuals who have AIDS (especially those individuals with extremely low CD4 counts). Yakrus et al. (J. Clin. Microbiol., 28:926–929, (1990)) identified MAC organisms that were most frequently associated with disseminated disease: *M. avium* serovar 4 (40%), *M. avium* serovar 8 (17%), non-typeable MAC (13%), and *M. avium* serovar 1 (9%).

Laboratory diagnosis of disseminated MAC traditionally has been based on culture methodology. MAC culture methods are labor, material, and resource intensive, and require relatively long periods of time for definitive diagnosis. Because of this, a polymerase chain reaction (PCR) test for the detection of MAC infection would be advantageous.

PCR-based amplification of target nucleic acids allows rapid and sensitive detection of target DNA sequences. Amplified sequences accumulate to concentrations that are easily detected using non-isotopic detection methods. PCR technology theoretically allows the practitioner to identify a specific target nucleic acid in samples which may contain just a single target.

Kulski et al. (J. Clin. Microbiol., 33:668, (1995)) investigated the use of multiplex PCR to detect members of the Mycobacterium genus and to detect and differentiate *M. tuberculosis*, *M. avium*, and *M. intracellulare*. These investigators coamplified regions of the 16s rRNA gene with a region of the MPB70 gene to detect and differentiate *M. avium*, *M. intracellulare*, and *M. tuberculosis*.

Abed et al. (Res. Microbiol., 146:405, 1995) amplified the entire 16s to 23s rRNA spacer region and used a secondary technique of RAPD fingerprinting to differentiate 56 strains belonging to 11 Mycobacterium species. Their PCR primers resided outside the intergenic region, with their forward and reverse primers targeted to the 16s rRNA gene and the 23s rRNA gene, respectively.

Barry et al. (EP Publication No. 0395292), and Rossau et al. (EP Publication No. 0525095), describe amplification of the entire 16s to 23s intergenic region, and diagnostic tests for bacterial organisms using probes targeted for sequences within the 16s to 23s intergenic region. As in Abed et al., the primers used by Barry et al. and Rossau et al. were targeted for sequences located within the genes encoding 16s or 23s rRNA.

Booth et al. (Infection and Immunity, 61(4):1509, (1993)) found a high degree of similarity between the 19 kd protein genes of *M. avium*, *M. tuberculosis*, and *M. intracellulare*. This high degree of similarity at the level of the gene persists at the protein level. Nair et al. (Molecular Microbiology, 6(11):1431, (1992)) demonstrated that the *M. intracellulare* gene encodes a seroactive lipoprotein. This lipoprotein was considered to be the *M. intracellulare* homologue of the serologically active 19 kd *M. tuberculosis* protein.

In designing assays to detect the presence of the MAC, the skilled artisan is faced with a significant challenge in selecting primer and probe combinations that detect all of the organisms that comprise the MAC and that do not cross react with non-MAC organisms. The present invention overcomes these problems by providing primers and probes specific for organisms of the MAC that can be used to co-amplify at least two, and preferably three, gene regions of these organisms.

SUMMARY OF THE INVENTION

In one embodiment, the present invention relates to a method for amplifying nucleic acids from MAC organisms. The method involves contacting a sample suspected of containing nucleic acids from MAC organisms with four different nucleoside triphosphates, a thermostable DNA polymerase, and a set of oligonucleotide primers specific for two or more of the following three gene regions: MacSequevar gene region, *M. avium* 19 kilodalton protein gene region, and *M. intracellulare* ribosomal protein sl gene region, under conditions such that the nucleic acids are amplified.

In another embodiment, the present invention relates to a method for amplifying and detecting nucleic acids from MAC organisms. The method involves contacting a sample suspected of containing nucleic acids from MAC organisms with four different nucleoside triphosphates, a thermostable DNA polymerase, and a set of oligonucleotide primers specific for two or more of the following three gene regions:

MacSequevar gene region, M. avium 19 kilodalton protein gene region, and M. intracellulare ribosomal protein sl gene region, under conditions such that the nucleic acids are amplified. The amplified product is then denatured and detected.

In a further embodiment, the present invention relates to a method for detecting and distinguishing M. avium from other organisms of the Mycobacterium avium complex comprising contacting a sample suspected of containing nucleic acids from organisms of the MAC with an oligonucleotide probe comprising nucleotide sequence: 5' CCC TGA GAC AAC ACT DGG TCC GTC C 3' (SEQ ID NO:1), wherein D is any nucleotide other than C and detecting the presence present invention, specific gene regions of the MAC genome are amplified by contacting a biological sample suspected of containing nucleic acids of such organisms with primer sets specific for two or more of the three gene regions. Preferably primer sets specific for all three gene regions are used to co-amplify the three regions. In addition to the primers, the biological sample is also contacted with PCR reagents, such as four different nucleoside triphosphates and a thermostable DNA polymerase, under conditions such that any MAC organism present in the sample will have its target nucleic acid amplified. Examples of primers suitable for use in the present invention include, but are not limited to, those shown below in Table 1.

TABLE 1

| Primer/Probe | Sequence | |
| --- | --- | --- |
| MSqv F4 | 5' GTG CGC AAC AGC AAA TGA TTG GGA GAC A 3' | (SEQ ID NO:2) |
| MSqv F2 | 5' TGC ACA ACA GCA AAT GAT TGC CAG ACA C 3' | (SEQ ID NO:3) |
| MSqv R5 | 5' CCA CCA AGA TGG AGG GAC TCC ACA 3' | (SEQ ID NO:4) |
| MSqv R2 | 5' CCA ATA CTC AAA CAC CAC ACC CCA CCA CCA A 3' | (SEQ ID NO:5) |
| MSqv-Av | 5' CCC TGA GAC AAC ACT GGG TCC GTC C 3' | (SEQ ID NO:6) |
| MSqv P1.21c | 5' CCC TGA GAC AAC ACT CGG TCC GTC C 3' | (SEQ ID NO:7) |
| MSqv-MAC | 5' CCC TGA GAC AAC ACT CGG TCG GTC C 3' | (SEQ ID NO:8) |
| MSqv P1 | 5' G CCC TGA GAC AAC ACT CGG TCA GTC 3' | (SEQ ID NO:9) |
| MSqv 1.3c | 5' CCC TGA GAC AAC ACT CGG TCG ATC C 3' | (SEQ ID NO:10) |
| MAV19K F1 | 5' CGG CTG TTC GAG TGG CAA CAA GTC 3' | (SEQ ID NO:11) |
| MAV19K R1 | 5' CCG TCG ATG ATG ACC TTG GTC CC 3' | (SEQ ID NO:12) |
| MAV19K P1 | 5' AGT CCG TCG GCG AGC AGC GG 3' | (SEQ ID NO:13) ‖ |
| rpsl F1 | 5' CGG GAC AAG GTC GCC AAG GTC AAG A 3' | (SEQ ID NO:14) |
| rpsl R1 | 5' GGG ATG TAG GCC GTC ACC TCA AC 3' | (SEQ ID NO:15) |
| rpsl P1 | 5' GAC CTT CCG AAG AGC GGA GTT CG 3' | (SEQ ID NO:16) | or absence of a complex formed between the probe and nucleic acids present in the sample.

Various other objects and advantages of the present invention will be apparent from the detailed description of the invention.

All publications mentioned herein are hereby incorporated by reference.

DETAILED DESCRIPTION OF THE INVENTION

The development of a nucleic acid co-amplification system that detects all MAC organisms without crossreacting with non-MAC mycobacteria is very challenging. Applicants have overcome several obstacles to arrive at the present invention relating to the amplification and/or detection of nucleic acids from MAC organisms.

In the present invention, three gene regions have been identified that are compatible with each other in a multiplexed system and can, therefore, be used in co-amplification assays to amplify nucleic acids from MAC organisms. These three gene regions are the MacSequevar region (Msqv) found in M. avium, M. intracellulare, and non-M. avium, non-M. intracellulare MAC organisms, the M. avium 19 kilodalton protein (MAV19k), and the M. intracellulare ribosomal protein sl gene (rpsl). Using primers specific for two or more of these regions, amplification can be carried out in a multiplexed fashion in the presence of an internal positive control (IPC) that allows detection of false negative results due to problems in sample preparation, amplification and/or detection.

The present invention relates to methods for amplifying nucleic acids from MAC organisms. In the methods of the Other primer sets specific for the three gene regions of interest could be readily determined by those skilled in the art.

Once the nucleic acids of the MAC are amplified, the presence or absence of the amplified target nucleic acids can be detected using known detection methods. For example, the amplified target nucleic acid can be detected using oligonucleotide probes specific for the amplified gene regions. Those skilled in the art can readily identify oligonucleotide probes that would be suitable to detect the amplified gene regions given the primer sets used. Oligonucleotide probes suitable for use in the present invention include, but are not limited to the oligonucleotides set forth in Table 1.

The present invention also relates to methods of detecting and distinguishing M. avium from other organisms of the MAC. This is achieved by contacting a sample suspected of containing nucleic acids of MAC organisms with a probe comprising the nucleotide sequence:
5' CCC TGA GAC AAC ACT DGG TCC GTC C 3' (SEQ ID NO:1) ,
wherein D is any nucleotide other than C. Preferably, D is G or U. Such probes are specific to the 16s to 23s rRNA intergenic region and are M. avium specific. The single base change from C to any other nucleotide alters the specificity of the probe making it highly specific for M. avium.

The general principles and conditions for amplification and detection of nucleic acids using polymerase chain reaction (PCR) are quite well known, the details of which are provided in numerous references including U.S. Pat. Nos 4,683,195 (Mullis et al.), 4,683,202 (Mullis), and 4,965,188 (Mullis et al.), all of which are incorporated herein by reference. Thus, in view of the teaching in the art and the specific teaching provided herein, a worker skilled in the art should have no difficulty in practicing the present invention by co-amplifying two or more gene regions of organisms of the MAC to detect disseminated *M. avium* complex.

The term "oligonucleotide" refers to a molecule comprised of one or more deoxyribonucleotides or ribonucleotides, such as primers, probes, and nucleic acid fragments to be detected.

The term "primer" refers to an oligonucleotide, whether naturally occurring or synthetically produced, that is capable of acting as a point of initiation of synthesis when placed under conditions in which synthesis of a primer extension product complementary to a nucleic acid strand (that is, template) is induced, such conditions include the presence of other PCR reagents, and suitable temperature and pH.

The primer is preferably single stranded for maximum efficiency in amplification, but can contain a double stranded region if desired. It must be long enough to prime the synthesis of extension products in the presence of the DNA polymerase. The exact size of each primer will vary depending upon the use contemplated, the concentration and sequence of the primer, the complexity of the targeted sequence, the reaction temperature, and the source of the primer. Generally, the primers used in this invention will have from 12 to 60 nucleotides, and preferably, they have from 16 to 40 nucleotides. More preferably, each primer has from 18 to 35 nucleotides.

Primers useful herein can be prepared using known techniques and equipment, including for example an ABI DNA Synthesizer (available from Applied Biosystems) or a Biosearch 8600 Series or 8800 Series Synthesizer (available from Milligen-Biosearch, Inc.). Procedures for using this equipment are well known and described for example in U.S. Pat. No. 4,965,188 (Gelfand et al.), incorporated herein by reference. Naturally occurring primers isolated from biological sources may also be useful (such as restriction endonuclease digests).

As used herein, a "probe" is an oligonucleotide which is substantially complementary to a nucleic acid sequence of the target nucleic acid and which is used for detection or capture of the amplified target nucleic acid.

In the present invention, sequence specific primers and probes are provided. It will be apparent to those skilled in the art that additional sequence specific primers and probes can be prepared by, for example, the addition of nucleotides to either the 5' or 3' ends, which nucleotides are complementary or noncomplementary to the target sequence. Such compositions are within the scope of this invention.

The primers and/or the probes used in the present invention can, optionally, be labeled. Using known methods in the art, the primers and/or probes can be labeled with a specific binding ligand (such as biotin), an enzyme (such as glucose oxidase, peroxidases, uricase, and alkaline phosphatase), radioisotopes, electron-dense reagents, chromogens, fluorogens, phosphorescent moieties or ferritin. Preferably, the label is a specific binding ligand. More preferably, the label is biotin or a derivative thereof, streptavidin or a derivative thereof or a hapten.

A "PCR reagent" refers to any of the reagents considered essential for PCR, namely a set of primers for each target nucleic acid, a DNA polymerase (preferably a thermostable DNA polymerase), a DNA polymerase cofactor, and one or more deoxyribonucleoside-5'-triphosphates (dNTP's). Other optional reagents and materials used in PCR are described below. These reagents can be provided individually, as part of a test kit, or in reagent chambers of test devices.

A DNA polymerase is an enzyme that will add deoxynucleoside monophosphate molecules to the 3'-hydroxy end of the primer in a complex of primer and template, but this addition is in a template dependent manner. Generally, synthesis of extension products proceeds in the 5' to 3' direction of the newly synthesized strand until synthesis is terminated. Useful DNA polymerases include, for example, *E. coli* DNA polymerase I, T4 DNA polymerase, Klenow polymerase, reverse transcriptase and others known in the art. Preferably, the DNA polymerase is thermostable meaning that it is stable to heat and preferentially active at higher temperatures, especially the high temperatures used for priming and extension of DNA strands. More particularly, thermostable DNA polymerases are not substantially inactive at the high temperatures used in polymerase chain reactions as described herein. Such temperatures will vary depending on a number of reaction conditions, including pH, nucleotide composition, length of primers, salt concentration and other conditions known in the art.

A number of thermostable DNA polymerases have been reported in the art, including those mentioned in detail in U.S. Pat. Nos. 4,965,188 (Gelfand et al.) and 4,889,818 (Gelfand et al.), both incorporated herein by reference. Particularly useful polymerases are those obtained from various Thermus bacterial species, such as *Thermus aquaticus, Thermus thermophilus, Thermus filiformis,* and *Thermus flavus*. Other useful thermostable polymerases are obtained from various microbial sources including *Thermococcus literalis, Pyrococcus furiosus,* Thermotoga sp. and those described in WO-A-89/06691 (published Jul. 27, 1989). Some useful thermostable polymerases are commercially available, such as, AmpliTaq®, Tth, and UlTma® from Perkin Elmer, Pfu from Stratagene, and Vent and Deep-Vent from New England Biolabs. A number of techniques are also known for isolating naturally-occurring polymerases from organisms, and for producing genetically engineered enzymes using recombinant techniques.

A DNA polymerase cofactor refers to a nonprotein compound on which the enzyme depends for activity. Thus, the enzyme is catalytically inactive without the presence of cofactor. A number of materials are known cofactors including, but not limited to, manganese and magnesium salts, such as chlorides, sulfates, acetates and fatty acids salts. Magnesium chlorides and sulfates are preferred.

Also needed for PCR are two or more deoxyribonucleoside-5'-triphosphates, such as two or more of dATP, dCTP, dGTP, dTTP and dUTP. Analogues such as dITP and 7-deaza-dGTP are also useful. Preferably, the four common triphosphates (dATP, dCTP, dGTP and dTTP) are used together.

The PCR reagents described herein are provided and used in PCR in suitable concentrations to provide amplification of the target nucleic acid. The minimal amounts of primers, DNA polymerase, cofactors and deoxyribonucleoside-5'-triphosphates needed for amplification and suitable ranges of each are well known in the art. The minimal amount of DNA polymerase is generally at least about 0.5 units/100 $\mu$l of solution, with from about 2 to about 25 units/100 $\mu$l of solution being preferred, and from about 7 to about 20 units/100 $\mu$l of solution being more preferred. Other amounts may be useful for given amplification systems. A "unit" is defined herein as the amount of enzyme activity required to incorporate 10 nmoles of total nucleotides (dNTP's) into an extending nucleic acid chain in 30 minutes at 74° C. The minimal amount of primer is at least about 0.075 $\mu$molar with from about 0.1 to about 2 $\mu$molar being preferred, but other amounts are well known in the art. The cofactor is generally present in an amount of from about 2 to about 15 mmolar. The amount of each dNTP is generally from about 0.25 to about 3.5 mmolar.

The PCR reagents can be supplied individually, or in various combinations, or all in a buffered solution having a pH in the range of from about 7 to about 9, using any suitable buffer, many of which are known in the art.

Other reagents that can be used in PCR include, for example, antibodies specific for the thermostable DNA polymerase. Antibodies can be used to inhibit the polymerase prior to amplification. Antibodies useful in the present invention are specific for the thermostable DNA polymerase, inhibit the enzymatic activity of the DNA polymerase at temperatures below about 50° C., and are deactivated at higher temperatures. Useful antibodies include, monoclonal antibodies, polyclonal antibodies and antibody fragments. Preferably, the antibody is monoclonal. The antibodies useful in the present invention can be prepared using known methods such as those described in Harlow et al., Antibodies: A Laboratory Manual, Cold Spring Harbor, N.Y. (1988).

Representative monoclonal antibodies are described in U.S. Pat. No. 5,338,671 (Scalice et al.), the contents of which are hereby incorporated by reference. Two such monoclonal antibodies are readily obtained by a skilled artisan using conventional procedures, and starting materials including either of hybridoma cell lines HB 11126 or 11127, deposited with the American Type Culture Collection (ATCC) (Rockville, Md.). The monoclonal antibody is present in an amount of from about 5:1 to about 500:1 molar ratio to the DNA polymerase.

A target nucleic acid, including that from a MAC organism, can be obtained from any of a variety of sources such as peripheral blood mononuclear cells (PBMC's), whole blood, respiratory fluids, lymph, and stool. Generally, it is extracted in some conventional manner to make it available for contact with the primers and other PCR reagents. If the target nucleic acid is double stranded, the two strands must be separated before priming can occur. Denaturation can be accomplished using any of the known techniques such as heat treatment, physical treatment or chemical treatment.

Amplification is preferably conducted in a continuous, automated manner so that the reaction mixture is temperature cycled in a controlled manner for desired preset times. A number of instruments have been developed for this purpose and are available to those skilled in the art. Preferably, amplification is carried out in a closed reaction vessel, such as the chemical test pack described in U.S. Pat. No. 5,229,297, which vessel is processed on the instrument described in U.S. Pat. No. 5,089,233.

Amplified nucleic acids can be detected in a number of known ways, such as those described in U.S. Pat. No. 4,965,188 (Gelfand et al.). For example, the amplified nucleic acids can be detected using Southern blotting, dot blot techniques, or nonisotopic oligonucleotide capture detection with a labeled probe. Alternatively, amplification can be carried out using primers that are appropriately labeled, and the amplified primer extension products can be detected using procedures and equipment for detection of the label.

In a preferred embodiment, the amplified target nucleic acid is detected using an oligonucleotide probe that is labeled for detection and can be directly or indirectly hybridized with the amplified target. The probe may be soluble or attached to a solid support. When multiple probes are used in the present invention, the probes can be attached to a solid support at different locations. Alternatively, the probes can be attached to the solid support as a mixture at the same location. In another preferred embodiment, one or more of the primers used to amplify the target nucleic acid is labeled, for example, with a specific binding moiety. The resulting primer extension product into which the labeled primer has been incorporated can be captured with a probe. Detection of the amplified target hybridized to the probe can be achieved by detecting the presence of the labeled probe or labeled amplified target using suitable detection equipment and procedures that are well known in the art. Certain labels may be visible to the eye without the use of detection equipment.

In a more preferred embodiment, one or more of the primers used to amplify the target nucleic acid is labeled with biotin and the biotinylated amplified target nucleic acids are hybridized to probes attached to a solid support. The bound targets are then detected by contacting them with a streptavidin-peroxidase conjugate in the presence of an oxidant, such as hydrogen peroxide, and a suitable dye-forming composition. For example, useful dye-providing reagents include tetramethylbenzidine and derivatives thereof, and leuco dyes, such as triarylimidazole leuco dyes as described in U.S. Pat. No. 4,089,747 (Bruschi).

Preferably, amplification and detection are carried out in a closed reaction vessel to reduce the risk of contamination. Both amplification and detection can be carried out in a closed reaction vessel as described in U.S. Pat. No. 5,229,297, without opening up the reaction vessel during the process.

As used herein, when in reference to time the term "about" refers to +/−10% of that time limit. When used in reference to temperatures, the term "about" refers to +/−5° C.

The following Examples are provided to illustrate certain embodiments of the present invention, and are not to be construed as limiting the invention.

EXAMPLES

The following primers and probes were used to detect the organisms of MAC and to differentiate *M. avium, M. intracellulare* and non-*M. avium,* non-*M. intracellulare* MAC organisms.

| Primer/Probe | |
|---|---|
| MSqv F4 | (SEQ ID NO:2) |
| MSqv F2 | (SEQ ID NO:3) |
| MSqv R5 | (SEQ ID NO:4) |
| MSqv R2 | (SEQ ID NO:5) |
| MSqv-Av | (SEQ ID NO:6) |
| MSqv P1.21c | (SEQ ID NO:7) |
| MSqv-MAC | (SEQ ID NO:8) |
| MSqv P1 | (SEQ ID NO:9) |
| MSqv 1.3c | (SEQ ID NO:10) |
| MAV19K F1 | (SEQ ID NO:11) |
| MAV19K R1 | (SEQ ID NO:12) |
| MAV19K P1 | (SEQ ID NO:13) \|\| |
| rpsl F1 | (SEQ ID NO:14) |
| rpsl R1 | (SEQ ID NO:15) |
| rpsl P1 | (SEQ ID NO:16) |

| Oligonucleotide | Type | Length | % GC | Tm[b] |
|---|---|---|---|---|
| MSqv F4 | Forward | 28-mer | 50 | 70.4 |
| MSqv F2 | Forward | 28-mer | 46.4 | 69.2 |
| MSqv R5 | Reverse | 24-mer | 58.3 | 70.9 |
| MSqv R2 | Reverse | 31-mer | 51.6 | 72.3 |
| MSqv-Av | Probe | 25-mer | 64 | 72.3 |
| MSqv P1.21c | Probe | 25-mer | 64 | 72.3 |
| MSqv-MAC | Probe | 25-mer | 64 | 72.3 |
| MSqv P1 | Probe | 25-mer | 60 | 72.1 |

-continued

| | | | | |
|---|---|---|---|---|
| MSqv 1.3c | Probe | 25-mer | 60 | 72.1 |
| MAV19K F1 | Forward | 24-mer | 58.3 | 70.9 |
| MAV19K R1 | Reverse | 23-mer | 60.9 | 71 |
| MAV19K P1 | Probe | 20-mer | 75 | 73.3 |
| rpsl F1 | Forward | 25-mer | 57.6 | 72.1 |
| rpsl R1 | Reverse | 23-mer | 60 | 71 |
| rpsl P1 | Probe | 23-mer | 60.8 | 71 |

Primers and probes were constructed to the following target gene regions:

1) MacSequevar region (MSqv) (16S–23S intergenic region)
2) *M. avium* 19 Kilodalton Protein Gene Region (MAV19k)
3) *M. intracellulare* ribosomal protein sl gene (rpsl)

The primers selected from the MSqv region allow specific amplification of nucleic acids from *M. avium, M. intracellulare* and all other MAC organisms not classified as *M. avium* or *M. intracellulare* (non-*M. avium,* non-*M. intracellulare* MAC organisms). Once amplified, target nucleic acids from these organisms can be detected using one of the probes MSqv-P1.21c, MSqv-MAC, MSqv P1, or MSqv 1.3c. In addition, the probe MSqv-Av, which detects only *M. avium,* can be used to distinguish *M. avium* from *M. intracellulare* and from other non *M. avium* MAC organisms. The MAV19k primers and probe are specific for nucleic acids from *M. avium* while the rpsl primers and probe are specific for nucleic acids from non-*M. avium* MAC organisms, typically *M. intracellulare.*

The primers and probes were prepared using known starting materials and procedures using an Applied Biosystems Model 380B, three column DNA synthesizer using standard phosphoramidite chemistry and the ABI 1 μmolar scale, fast cycle protocol. Nucleoside-3'-phosphoramidites and nucleoside derivatized controlled pore glass supports were obtained from Applied Biosystems. The primers had the sequences identified above. They were functionalized at the 5' end with two tetraethylene glycol spacers followed by a single commercially available DuPont biotin phosphoramidite. The probes were functionalized at the 3' end with two tetraethylene glycol spacers followed by a single aminodiol linking group according to U.S. Pat. No. 4,914,210. All purifications were carried out using a nucleic acid purification column, followed by reversed phase HPLC techniques.

PCR Assay Conditions:

PCR amplification and detection were carried out using a Johnson & Johnson Clinical Diagnostics, Inc. processor and contained pouch system described in U.S. Pat. Nos. 5,089,233, 5,380,489 and 5,229,297. A two-step PCR process was used whereby the anneal/extension temperature for the PCR amplification of target DNA was set at 70° C. for 40 sec. and the denaturation temperature was set at 96° C. for 5 seconds. Forty cycles were used to amplify the target after which the PCR blister, containing the reaction mixture was heated to 103° C. for 2 min. to inactivate Taq polymerase.

| PCR Mix: | |
|---|---|
| magnesium chloride (mM) | 4 |
| primers (μM), each | 0.4 |
| glycerol level (% v/v) | 9.5 |
| dNTP's (total mM) (dATP, dCTP, dGRP and dTTP - 0.3 mM each) | 1.2 |

-continued

| PCR Mix: | |
|---|---|
| background (Calf Thymus) DNA (μg/reaction) | 5 |
| Taq mAb blend (molar ratio to Taq) | 55:1 |
| Taq polymerase (units/75 μL reaction) | 12 |
| positive control target (copies/rxn) | 10 |
| TRIS-Hcl (mM) | 18 |
| potassium chloride (mM) | 54 |
| Type IV gelatin (μg/ml) | 108 |
| EDTA (mM) | 0.725 |
| Tween 20 | 0.02% |

The monoclonal antibodies used in the PCR mix were a mixture of TP1-12.2 and TP4-9.2, which are specific for DNA polymerase from *Thermus acquaticus.*

These antibodies are described in more detail in U.S. Pat. No. 5,338,671.

Recombinant DNA polymerase from *T. acquaticus* was prepared using, known procedures, such as that described in EP-A-0 482 714, and had an activity of about 250,000 units/mg of protein.

When the PCR amplification of target was completed, the amplified product was allowed to hybridize to distinct target specific capture probes which were bound to 4–7 separate probe bead spots. Each spot consisted of unique capture probes covalently attached to (approx.) 1 micron polystyrene beads. The capture probes were attached to particles of poly[styrene-co-3-(p-vinylbenzylthio)propionic acid] (95:5 molar ratio, 1 μm average diameter) in the following manner. A suspension of the particles in water was washed twice with 2-(N-morpholino)ethanesulfonic acid buffer (0.1 molar, pH 6), and suspended to approximately 10% solids. A sample (3.3 ml) of the washed particles, diluted to 3.33% solids in the buffer (0.1 molar), was mixed with 1-(3-dimethylaminopropyl)-3-ethylcarbodiimide hydrochloride (2.1 ml of 84 mg/ml water) and the appropriate probe (983 μl of 44.44 OD/ml nanopure water). The resulting suspension was heated at 50° C. in a water bath for about two hours with intermittent mixing and centrifuged. The particles were washed three times with tris(hydroxymethyl-)aminomethane buffer (0.01 molar, pH 8) containing (ethylenedinitrilo)tetraacetic acid disodium salt (0.0001 molar) and resuspended therein to 4% solids. They were then diluted to 2% solids and mixed with 0.2% of poly [methyl acrylate-co-2-acrylamido-2-methylpropanesulfonic acid, sodium salt-co-2-acetoacetoxyethyl methacrylate] (90:4:6 weight ratio) for application to a heat sealable polyethylene polyester laminate (treated by corona discharge) in test devices prepared as described in WO-A-92/16659.

Hybridization of product to probe occurred at 58° C. The hybridization step was followed by the addition of streptavidin horseradish peroxidase (SA-HRP) (which binds to biotinylated product), followed by a wash step, and finally followed by the addition of a leuco dye. Dye intensity was assessed instrumentally (as delta Dr, reflection density) or by visual scoring.

| Streptavidin - peroxidase conjugate solution: | |
|---|---|
| 3-[N-Morpholino]propane sulfonic acid (mM) 100 | |
| NaH₂PO₄ (mM) | 29 |
| NaCl (mM) | 75 |

-continued

| | |
|---|---|
| 4' hydroxy acetanilide (mM) | 10 |
| Casein (Sigma Technical Grade) (mg/ml) | 5 (0.5%) |
| Wash Mix: | |
| NaH$_2$PO$_4$ (mM) | 29 |
| NaCl (mM) | 373 |
| Decyl Sodium Sulfate (mM) | 25 |

Leuco-dye Dispersion:

Visual color scores were determined by comparing the bead spot color to a standardized color chart. Visual color scores were given a value that related to the intensity of the blue color ("8" being a high positive score, and "0" being a negative score). A visual color score between "0" and "2" was designated negative. A visual color score greater than 2 and less than 4 was considered to be a questionable (low) positive. A color score between 4 and 8 was designated positive.

Other reagents and materials were obtained either from commercial sources or prepared using readily available starting materials and conventional procedures.

Example 1

Primer and Probe Selection

A. Minimization of Side Product Formation

Coamplification of target nucleic acids using multiple primer sets often is problematic. Primer interactions manifested in side-product formation such as primer-dimers and other "zero-cycle" artifacts can result in reduced amplification efficiency and assay sensitivity. Once primers were selected based on sequence homology to target nucleic acids and computer analysis using "Oligo" (National BioSciences, Inc. Plymouth, Minn.), various combinations of primers were tested (in the absence of target) to determine if the formation of detectable side products would occur. In general, pairwise combinations of primers were initially tested using standard PCR conditions, to determine if any primer combination was prone to producing primer dimer, or other non-desirable side products that would compete with the specific product of choice.

Based on results obtained from the aforementioned pairwise primer combinations, preferred primers and primer pairs were used to determine if the PCR master mix could be stored at room temperature for extended periods of time without forming undesirable side products. Complete PCR mix was prepared that contained the proper salts, glycerol, taq polymerase, taq antibody, calf thymus DNA, magnesium chloride, and primers. Multiplexed primer sets were used in each of the following combinations: Msqv F4/R5, Mav 19k F1/R1, IPC F1/R1 or Msqv F2/R5, Mav 19k F1/R1, IPC F1/R1. The complete PCR mix was stored at room temperature either in the presence or absence of purified target DNA (within the pouch for 0, 4 and 8 hours.

At the appropriate time points, the PCR reactions were performed using a pouch processor. Amplified product was electrophoresed in one percent agarose gels which were then stained with ethidium bromide (Sigma Chemical, St. Louis, Mo.) to identify amplification efficiency of the PCR reaction. The primer combination of MSqv F4/R5, MAV19k F1/R1, and IPC F1/R1 showed minimal to no side product formation when the PCR mix was incubated from 2 to 8 hours at room temperature prior to processing.

B. Primer Combination Selection for Coamplification

Five different anneal/extension temperatures were used to determine conditions which maximize target specific product formation and minimize side product formation. Primer sets were identified where product detection scores were equivalent, whether used as a single primer pair or when multiplexed with other primer pairs (based on gel electrophoresis of product and ethidium bromide staining) (Table 2). The preferred primer sets were those that gave strong product (gel bands) over the broadest anneal/extension temperature range. Each processor was set at a different anneal/extension temperature, and the temperature at which target was no longer amplified was determined. The combined (multiplexed) primers that best matched the (individual) primer anneal/extension temperature performance were selected for further testing. PCR mixes were prepared as mentioned in Example 1A. The multiplexed primer combination of Msqv F4/R5, Mav 19k F1/R1, IPC F1/R1 was compared with Msqv F2/R5, Mav 19k F1/R1, IPC F1/R1 to determine if either Msqv forward primer would allow more robust amplification than the other with respect to equivalent PCR (gel band) signal for each anneal/extent temperature setting. Four replicate pouches of each multiplexed system were run on each pouch processor.

TABLE 2

Amplification Efficiency at Different Anneal/Extension Temperatures

| Temp | Msqv F4/R5 | 19k F1/R1 | IPC F1/R1 | Msqv F2/R5 | 19k F1/R1 | IPC F1/R1 |
|---|---|---|---|---|---|---|
| 68° C. | + | + | w | + | + | w |
| 69 | + | + | w | + | + | w |
| 70 | + | + | w | + | + | w |
| 71 | + | + | − | + | + | − |
| 72 | w | + | − | w | + | − |

(+) strong gel band;
(w) weak gel band;
(−) no gel band observed

Targets used were *M. avium* (strain A4, serovar 4) 20 copies/test, 10 copies IPC/test. Two alternative multiplexed MAC assay systems are shown in Table 2; MSqv F4/R5, 19k F1/R1, IPC F1/R1 and MSqv F2/R5, 19k F1/R1, IPC F1/R1.

The anneal/extend temperature where each system failed to amplify target was shown to be greater than or equal to 72° C., alternatively, the internal positive control did not amplify its target beyond 70° C. The MAC-specific primer systems performed sufficiently over a broad range of anneal/extension temperatures (68° C.–71° C.).

Example 2

Sensitivity of the MAC Assay

The PCR-based MAC assay was shown to have single gene copy sensitivity. Cesium chloride purified DNA samples from *M. avium* and *M. intracellulare* were acquired from T. Hellyer (Univ. Arkansas, Little Rock) for the experiments of example 2. The DNA contained in these samples was quantitated using absorption spectrophotometry, and the purity was determined by calculating the A260/A280 absorption ratio. A ratio of 1.8 or greater is indicative of highly purified DNA. The number of genomes/µL of sample was estimated based on the value of 10 femtograms of DNA per mycobacterial genome. All target genes for this MAC assay were found as single copy genes so that a single organism contained one copy of target per genome. This purified DNA was diluted in TRIS-EDTA buffer, pH 8.5

(containing carrier, calf thymus, DNA at 10 µg/ml final concentration). Stock (target) DNA of between 10 million and 100 million genomes/µl was diluted to 0.5 copies/µl so that when 20 µl of this stock was used in PCR the resulting copy number of target per test would be 10 copies. Three additional 3.16 fold dilutions of 0.5 copies/µl were used to obtain 3.16, 1, and 0.316 copies target/test. The MAC assay was able to detect a single genome copy approximately 60% of the time (as would be anticipated assuming a Poisson sampling distribution), and 3 genome copies nearly 100% of the time.

TABLE 3

Sensitivity using *M. avium* DNA with Multiplexed MAC Assay in Pouch

| Target copies/test | # tests performed (n) | percentage of total tests run resulting in a positive-signal MSqv P1 | MAV19k P1 | IPC - 1P |
|---|---|---|---|---|
| 0 | 4 | 0 | 0 | 100% |
| 0.316 | 4 | 25% | 25% | 100% |
| 1 | 4 | 50% | 75% | 100% |
| 3.16 | 4 | 100% | 100% | 100% |
| 10 | 4 | 100% | 100% | 100% |

Table 3 shows the results of multiplexed pouch assays where the percentage of the tests that resulted in a positive signal was compared with the estimated average number of target DNA copies per sample (purified DNA was diluted in Tris/EDTA buffer containing carrier DNA) undergoing PCR amplification. MSqv P1, MAV19k P1, and IPC-1P (Internal Positive Control) probe bead spots were separately located within the detection blister of the pouch. Biotinylated product was bound to the target-specific probe bead spots. Bound product was determined using a streptavidin-HRP wash, a second wash to remove non-specific HRP, and finally followed by a leuco dye wash. Color generation occurred over the bead spots that contained probe-specific, PCR amplified, product. Purified target DNA was from *M. avium* isolate #177, serovar 2. Multiplexed PCR was performed using MSqv F4/R2 with MAV19k F1/R1 and IPC primers. Single gene copy sensitivity was observed with the *M. avium* isolate 177.

TABLE 4

Sensitivity using *M. intracellulare* DNA with Multiplexed MAC Assay in Pouch

| Target copies/test | # tests performed (n) | percentage of total tests run resulting in a positive signal MSqv P1 | rpsl P1 | IPC -1P |
|---|---|---|---|---|
| 0 | 6 | 0 | 0 | 100% |
| 0.316 | 10 | 10% | 10% | 100% |
| 1 | 10 | 60% | 40% | 100% |
| 3.16 | 10 | 100% | 80% | 100% |
| 10 | 10 | 100% | 100% | 100% |

Table 4 shows results of a multiplexed pouch assay for detection of *M. intracellulare* wherein MSqv P1, rpsl P1, and IPC-1P (Internal Positive Control) probe bead spots were separately located within the detection blister. The experimental protocol was identical to that of the experiment shown in Table 3 except for obvious variations. Purified target DNA was that of *M. intracellulare*, serovar 16 (ATCC 13950) provided by Kevin Nash (L.A. Children's Hospital, Los Angeles, Calif.). Purified DNA was obtained from whole organisms, which were heated at 100° C. for 30 min, and the DNA was purified using a standard phenol/chloroform procedure. Multiplexed PCR was performed using MSqv F4/R5 with rpsl F1/R1 and IPC primers. Single gene copy sensitivity was observed with the MSqv primer/probe set, but was approximately 5 times less sensitive with the rpsl primer and probe set.

Example 3

Sensitivity of the MAC Assay with *M. avium* Target DNA Derived From Multiple Isolates

*M. avium* target DNA from six (6) patient isolates was amplified according to the PCR protocol outlined above using two primer sets (MacSqv and MAV19k) followed by capture of product on separate target specific probe beads. CsCl purified DNA was supplied by T. Hellyer, University of Arkansas. The DNA from each organism was diluted and tested in the pouch system as previously described. Single gene copy sensitivity was obtained for each isolate using the MAC assay system as shown in Table 5A, and the corresponding 3 gene copy sensitivity as shown in Table 5B.

TABLE 5A

Comparing Single Gene Copy Sensitivity When Using Multiple Serovars of *M. avium*

| Isolate (Serovar) | A260/A280 ratio | n | % positive bead spots MSqv P1 | MAV19k P1 |
|---|---|---|---|---|
| B92 (1) | 1.74 | 5 | 40% | 60% |
| 177 (2) | 1.8 | 4 | 50% | 75% |
| A4 (4) | 1.8 | 4 | 50% | 50% |
| A7 (6) | 1.86 | 4 | 50% | 50% |
| A8 (8) | 1.98 | 4 | 100% | 75% |
| LR 131 (9) | 1.75 | 4 | 50% | 75% |

As shown in Table 5A, a positive result was observed approximately 60% of the time (as would be predicted by Poisson's statistics for a single gene copy). In every case, the percentage of tests resulting in a positive signal centered around 60%, indicating that the assay exhibited single gene copy sensitivity over a range of *M. avium* (serovars and) patient isolates. That 100% positive results for isolate A8 with the MSqv set was achieved would indicate this sample might contain slightly more than a single gene copy per test.

TABLE 5B

Comparing (3) Gene Copy Sensitivity When Using Multiple Serovars of *M. avium*

| Isolate (Serovar) | A260/A280 ratio | n | % positive bead spots MSqv P1 | MAV19k P1 |
|---|---|---|---|---|
| B92 (1) | 1.74 | 5 | 100% | 100% |
| 177 (2) | 1.8 | 4 | 100% | 100% |
| A4 (4) | 1.8 | 4 | 100% | 75% |
| A7 (6) | 1.86 | 4 | 100% | 100% |
| A8 (8) | 1.98 | 4 | 100% | 100% |
| LR 131 (9) | 1.75 | 4 | 100% | 100% |

Conditions for these experiments were the same as those of Table 5A. The target dilutions used were from the same serial dilution as in Table 5A. In this case, at roughly 3 genomic copies per test, we found 100% positive results. The only set that did not yield 100% positives was the MAV19k primer/probe set with patient isolate A4.

Example 4

Inclusivity Testing (Identifying Organisms Within the MAC)

Several strains from each serovar within the MAC were grown in-house, the cells were lysed by heating, and the DNA was purified using the polymer capture technique taught in our pending application U.S. application Ser. No. 08/306,870 (also see U.S. Pat. Nos. 5,434,270 and 5,523,368 relating to the monomer and polymer compositions and methods of preparation thereof). The resulting DNA was used as the target in PCR amplification tests with different combinations of MacSqv forward and reverse primer sets, either separately or in combination with MAV19k (or rpsl), or both and Internal Positive Control (IPC) primer sets. The tests were carried out with the target DNA levels between 10 and 5000 genomic copies per PCR reaction.

The inclusivity panel used to test MAC primers and probes is described below. MAC organisms are listed according to their serovar number. The corresponding sequevars are also listed. The sequevar terminology used in the tables was as follows: "na" indicates a sequevar was not determined. "Mav" indicates sequevars corresponding to *M. avium*. "Min" indicates sequevars corresponding to *M. intracellulare*. "MAC" indicates MAC sequevars that were classified as neither "Mav" nor "Min". Organisms with serovars 1 through 6, 8 through 11, and 21 are *M. avium*. Organisms with serovars 7, 12 through 20, and 22 through 26 were assumed to be either *M. intracellulare* or MAC organisms not belonging to either of the *M. avium* or *M. intracellulare* species according to Wayne et al., supra.

PCR amplification and detection were performed using the processor and self contained pouch system and conditions as described above. Product was captured with probes attached to beads as indicated in Table 6 along with the observed visual color scores.

TABLE 6

Inclusivity Panel: Using Multiplexed MAC-specific and *M. avium*-specific Primers and Probes

| Serovar | Sequevar | Sample ID | IPC-IP | MSqv-P1 | Mav19K-P1 |
|---|---|---|---|---|---|
| 1 | Mav-A | B-92 | 6.5 | 7 | 4.75 |
| 1 | Mav-A | 11907-300 | 8 | 8 | 6.5 |
| 2 | Mav-C | 2-6194 | 7 | 7.5 | 7.5 |
| 2 | Mav-A | 14141-1395 | 7.75 | 7.75 | 7.5 |
| 3 | na | 128 Germany | 7.75 | 8 | 7.5 |
| 4 | Mav-A | TMC 1463 | 7.75 | 7.5 | 7.75 |
| 5 | Mav-B | 25546-759 | 7.75 | 7 | 3.25 |
| 6 | Mav-A | 34540 | 7.75 | 7.75 | 3.75 |
| 7 | Min-A | 157 Manten | 7.5 | 8 | 0 |
| 7 | MAC-E | P49 | Not Tested | Not Tested | Not tested |
| 8 | Mav-B | SJB 2 | 7.5 | 7 | 7.5 |
| 9 | Mav-D | 1784-286 | 7* | 7* | 1* |
| 10 | Mav-B | TMC-1461 | 7.75 | 7.75 | 3.5 |
| 10 | Mav-B | 1602-1965 | 7.75 | 8 | 5 |
| 11 | Mav-A | TMC-1462 | 7.75 | 7.75 | 6.75 |
| 12 | Min-A | P-42 | 7.5 | 7.75 | 0 |
| 12 | Min-A | 6845 | 7.8 | 7.75 | 0 |
| 13 | Min-A | AlCC25122 | 8 | 8 | 0 |
| 14 | Min-A | Edgar-Boone | 7.25 | 7.5 | 0 |
| 15 | Min-A | TMC 1473 | 7.5 | 7.5 | 0 |
| 16 | Min-A | Yandel | 7.25 | 7.5 | 0 |
| 17 | Min-A | P-54 | 7 | 7.5 | 0 |
| 18 | MAC-D | Melnick | 7.5 | 7.75 | 0 |
| 19 | na | Darden | 7.75 | 8 | 0 |
| 19 | MAC-A | W552 | 7.25 | 6.5 | 0 |
| 20 | Min-A | TMC 1419 | 7.5 | 7.75 | 0 |
| 20 | na | AT 545 Findley | 7.75 | 8 | 0 |
| 21 | Max-B | 2993 | 6.75 | 6.75 | 7 |
| 22 | MAC-F | 5154 O'Connor | 6 | 7 | 0 |
| 23 | MAC-C | 23393 | 7.5 | 7.75 | 0 |
| ? | na | CDC 1217 | 7.5 | 7.5 | 0 |
| 24 | MAC-B | 12645 | 7.75 | 7.75 | 0 |
| 25 | na | CDC 1195 | 7.5 | 7.5 | 0 |
| 25 | Min-A | 72-888 | 7 | 7.25 | 0 |
| 26 | Min-A | Hilberry 1244 | 7.75 | 8 | 0 |

Table 6 shows the results obtained when MSqvF4/R5 and Mav 19k primers were combined with IPC primers in a multiplexed amplification/detection test format using of a MAC inclusivity panel. The MSqv primer set and the corresponding probe enable detection of all organisms within the MAC panel listed. The MSqv primer set also allowed exclusive detection of *M. avium* organisms within the panel when the *M. avium*-specific probe (MSqv-Av) was used in a multiplexed assay with MAV19k and IPC primers and probes (data not shown). The MAV19k set allowed detection of only *M. avium* organisms, but failed to allow detection of strain 1784-286. All results are based on duplicate pouch results except with strain 1784-286, where the results are based on a single pouch. (Although strain 1784-286 was not identified by MAV19k in the experiment corresponding to Table 6, it was identified in many other experiments).

TABLE 7

Inclusivity Panel: Using Multiplexed MAC-specific
M. avium-specific and M. intracellulare-specific
Primers and Probes

| Serovar | Sequevar | Strain | IPC-1P | MSqv-MAC | Mav19K-P1 | rps1-P1 |
|---|---|---|---|---|---|---|
| 1 | Mav-A | B-92 | 7.5 | 5.5 | 3.5 | 0 |
| 1 | Mav-A | 11907-300 | 7 | 4.25 | 4.5 | 0 |
| 2 | Mav-C | 2-6194 | 8 | 5.75 | 5 | 0 |
| 2 | Mav-A | 14141-1395 | 7.5 | 5.5 | 2.75* | 0 |
| 3 | na | 128 Germany | 8 | 6 | 5.25 | 0 |
| 4 | Mav-A | TMC 1463 | 8 | 6 | 2.75* | 0 |
| 5 | Mav-B | 25546-759 | 7.5 | 6 | 2.25* | 0 |
| 6 | Mav-A | 34540 | 7.5 | 6 | 5 | 0 |
| 7 | Min-A | 157 Manten | 7.75 | 6 | 0 | 6 |
| 7 | MAC-E | P49 | 7.25 | 6.5 | 0 | 0 |
| 8 | Mav-B | SJB2 | 8 | 6.25 | 4.25 | 0 |
| 9 | Mav-D | 1784-286 | 7.25 | 6 | 1.75* | 0 |
| 10 | Mav-B | TMC 1461 | 7.5 | 6.25 | 4.75 | 0 |
| 10 | Mav-B | 1602-1965 | 7 | 4.25 | 3* | 0 |
| 11 | Mav-A | TMC 1462 | 7 | 5.25 | 3.75 | 0 |
| 12 | Min-A | P-42 | 7.75 | 6 | 0 | 2.5* |
| 12 | Min-A | 6845 | 6.75 | 6 | 0 | 6 |
| 13 | Min-A | ATCC 25122 | 8 | 6.75 | 0 | 3.25* |
| 14 | Min-A | Edgar Boone | 7.5 | 6.5 | 0 | 5.25 |
| 15 | Min-A | TMC 1473 | 7.5 | 6.5 | 0 | 6 |
| 16 | Min-A | Yandel | 7.75 | 6 | 0 | 6.5 |
| 17 | Min-A | P-54 | 7.5 | 6.75 | 0 | 6.5 |
| 18 | MAC-D | Melnick | 6.25 | 6.5 | 0 | 1 |
| 19 | na | Darden | 7.25 | 6.5 | 0 | 6.5 |
| 19 | Mac-a | W552 | 7.75 | 5.25 | 0 | 6 |
| 20 | Min-A | TMC 1419 | 7 | 6 | 0 | 5 |
| 20 | na | AT 545 Findley | 7.25 | 5.5 | 0 | 5.5 |
| 21 | Mav-B | 2993 | 6.5 | 6 | 5 | 0 |
| 22 | MAC-F | 5154 O'Connor | 7.75 | 5.5 | 0 | 0 |
| 23 | MAC-C | 23393 | 7.75 | 5.5 | 0 | 5.25 |
| ? | na | CDC 1217 | 7 | 6 | 0 | 2.25* |
| 24 | MAC-B | 12645 | 7.75 | 6 | 0 | 4.5 |
| 25 | na | CDC 1195 | 7.75 | 6 | 0 | 6 |
| 25 | Min-A | 72-888 | 7.25 | 6 | 0 | 3.5* |
| 26 | Min-A | Hilberry 1244 | 7.25 | 6 | 0 | 4.75 |

Table 7 coamplification results obtained using the MSqv F2/R5 primer set with the MAV19K, rpsl and IPC primer sets. All color scores greater than two represent positive detection using the indicated probe. When this multiplexed system is used to identify organisms within the MAC-complex at the species level the MacSqv primer set (and MacSqv —MAC probe) identifies all organisms within the panel. The rpsl primer set (and probe) identifies all organisms considered to be M. intracellulare by previous investigators and the Mav19k primer set (and probe) identifies M. avium organisms within the panel.

Many ambiguous strains were represented on the inclusivity panel shown. For example, when Frothingham, 1993 (supra.), Saito, (supra.), and Wayne, 1993 (supra.) used DNA sequencing, Gen-Probe probes, HPLC, and/or biochemical methods to classify MAC reference strains by species, there were several strains that did not fit neatly into either category of M. avium or M. intracellulare. Therefore many of these strains were characterized as "MAC" organisms.

The following strains were identified by Wayne, 1993 (supra.) as M. intracellulare by HPCL analysis: 12645, 23393, Melnick, and 1217. These same strains were identified as M. intracellulare using the rpsl primer and probe set shown in Table 7, even though in the hands of the aforementioned investigators these same strains were Gen-Probe negative when using Gen-Probe M. intracellulare probe.

The following strains were identified as M. intracellulare by HPLC analysis and by Gen-Probe by the aforementioned investigators: W552, Darden, AT 545 Findley, CDC 1195. These strains were also identified as M. intracellulare by the rpsl system.

The remaining ambiguous strains P-49 and 5154 O'Connor were still unable to be properly characterized by the investigators cited above. In Table 7, these two strains are characterized as MAC organisms. Frothingham, 1993 (supra.) sequenced the 16s–23s internal transcribed spacer region and found that the gene sequences of these two strains were unlike those of M. avium or M. intracellulare.

The MAV19K system identified only M. avium organisms. Again, M. avium strain 1784-286 gave questionable results, (and was the same sample stock used in table 6.) All visual color score values are based on the average color score (for a specific probe bead) between two pouches. Asterisks indicate a large variance between the color scores of the two replicates. The MSqv system permitted detection of all organisms on the panel.

When performing a multiplexed assay that contains MacSqv, Mav 19k and rpsl primers and probes, organisms within the MAC complex can be properly identified at the species level, as M. avium, M. intracellulare, or non-M. avium, non M. intracellulare MAC.

Example 5

Exclusivity Testing (Determining With Nucleic Acids of Non-MAC Mycobacteria)

Many mycobacteria have a high degree of genomic homology. This poses a challenge in designing MAC-specific primers and probes. A DNA based assay for MAC should have high specificity for those organisms within the *M. avium* complex, and not for any non-MAC mycobacteria.

TABLE 8

Exclusivity Testing - Mycobacteria (other than MAC)

| | | MAC | *M avium* | |
|---|---|---|---|---|
| Probe Specificity -> | | Msqv P1 | *M. avium* Msqv-Av | MAV19k P1 |
| Organism | ID # | | | |
| *M. africanum* | ATCC 25420 | — | — | — |
| *M. asiaticum* | ATCC 25276 | — | — | — |
| *M. bovis* BCG | ATCC 35734 | — | — | — |
| *M. bovis* | ATCC 19210 | — | — | — |
| *M. celetum* | ATCC 51131 | — | — | — |
| *M. chelonae* | ATCC 35752 | — | — | — |
| *M. flavescense* | ATCC 14474 | — | — | — |
| *M. fortuitum* | ATCC 6841 | — | — | — |
| *M. genavense* | 4096 | — | — | — |
| *M. genavense* | 4782 | — | — | — |
| *M. genavense* | 2289 | — | — | — |
| *M. gordonae* | ATCC 14474 | — | — | — |
| *M. haemophilum* | Patient isolate TK01 | — | — | — |
| *M. haemophilum* | ATCC 33206 | — | — | — |
| *M. kansasii* | ATCC 12478 | — | — | — |
| *M. malmoense* | Patient isolate KJ* | — | — | — |
| *M. marinum* | ATCC 927 | — | — | — |
| *M. microti* | ATCC 19422 | — | — | — |
| *M. peragrinum* | ATCC 14467 | — | — | — |
| *M. phleii* | ATCC 354 | — | — | — |
| *M. scrofulaceum* | Lane 3081 (ser 27) | — | — | — |
| *M. scrofulaceum* | ATCC 19981 | — | — | — |
| *M. simiae* | ATCC 25275 | — | — | — |
| *M. smegmatis* | ATCC 14468 | — | — | — |
| *M. triviale* | ATCC 23292 | — | — | — |
| *M. xenopi* | ATCC 19250 | — | — | — |

*Obtained from Daniel Amsterdam, Ph.D., Erie County Medical Center, Buffalo, NY
(All other organisms were obtained from Kevin Nash, Ph.D., L.A. Children's Hospital, Los Angeles, CA)

Table 8 shows the results obtained when MSqvF4/R5, Mav 19k F1/R1, and IPC primers were challenged with DNA from $3 \times 10^8$ non-MAC mycobacteria/mL. Three probe-specific bead spots were separately located within the detection blister. MAV19k P1 and MSqv-Av are *M. avium* specific, and MSqv P1 is specific to all organisms within the MAC. None of the primer probe systems cross reacted with any mycobacteria other than those included within the *M. avium* Complex. The results are a compilation of two experiments. The original panel test (MAC 080196) was repeated using additional strains of *M. haemophilum* and *M. malmoense* (MAC 080296). Exclusivity results for the rpsl primer/probe system show no cross-reactivity with non-MAC mycobacteria.

TABLE 9

Exclusivity Testing - Other Bacteria Mycobacteria

| Organism | ID = | MSqvF4 R5 MSqv-P1 | MSqvF4 R5 MSqv-Av | Mav 19K F1 R1 Mav 19K-P1 |
|---|---|---|---|---|
| *Aeromonas hydrophila* | patient isolate | — | NA | NA |
| *Bordetella bronchioseptica* | patient isolate | — | NA | NA |
| *Bordetella pertussis* | patient isolate | — | NA | NA |
| *Candida albicans* | patient isolate | — | NA | NA |
| *Citrobacter freundii* | patient isolate | — | — | — |
| *Corynebacterium diptheriae* | patient isolate | — | — | — |
| *Cryptococcus neoformans* | patient isolate | — | — | — |
| *Eikenella corrodens* | patient isolate | — | — | — |
| *Enterobacter aerogenes* | patient isolate | — | — | — |
| *Enterobacter cloacae* | patient isolate | — | — | — |
| *Enterobacter faecalis* | ATCC 29212 | — | NA | NA |
| *Enterococcus faecium* | patient isolate | — | — | — |
| *Escherichia coli* | ATCC 25922 | — | — | — |
| *Klebsiella pneumoniae* | patient isolate | — | — | — |
| *Listeria monocytogenes* | patient isolate | — | — | — |
| *Neisseria gonorrhoeae* | ATCC 49226 | — | — | — |
| *Nocardia caviae* | patient isolate | — | NA | NA |
| *Pseudomonas aeruginosa* | patient isolate | — | — | — |
| *Salmonella typhemurium* | patient isolate | — | — | — |
| *Salmonella typhi* | ATCC 6539 | — | NA | NA |
| *Serratia marcescens* | patient isolate | — | — | — |
| *Staphylococcus aureus* | patient isolate | — | — | — |
| *Staphylococcus epidermidis* | patient isolate | — | — | — |
| *Stretococcus pneumomiae* | patient isolate | — | — | — |
| *Xanthomonas maltophilia* | patient isolate | — | — | — |
| *M. szulgai* | ATCC 35799 | — | — | — |
| *M. terrae* | ATCC 15755 | — | — | — |
| *M. thermoresistible* | ATCC 19527 | — | — | — |
| MTB (H37Rv) | ATCC 25177 | — | — | — |
| *M. avium* (2,000 copies/tst) | ATCC 25291 | 5 | 4.75 | 6.25 |

Table 9 shows the results obtained when MSqvF4/R5, Mav 19k F1/R1, and IPC primers were challenged with DNA from $3 \times 10^8$ organisms (other than mycobacteria) per mL. Non-mycobacterial DNA was not detected (*M. avium* was used as a control).

Example 6

Creation of an *M. avium*-specific Probe By Making a Single Base Substitution in a MAC-Specific Probe from the 3' end of MSqv-Av. The MSqv-Av probe was synthesized on two separate occasions, and each new synthesis was tested against a panel of MAC organisms. In each case, the single base ("C" to "G") change altered the probe sufficiently that a previously broadly (MAC) specific probe was converted into a highly specific probe that only recognized target DNA from organisms of the species *M. avium*. A third synthesis whereby a "U" was used to replace the "C" in this same position resulted in an Avium-only specificity as well. This would suggest that the 25 nt probe (e.g. pl.21C)

FIG. 3
Sequence Comparison of 25 nt Probes

|  |  | Tm | Specificity |
|---|---|---|---|
|  | 132 137 138 |  |  |
| P1    5' GCCC CTG AGA CAA CAC TCG GTC AGT C 3' | (SEQ ID NO:9) | 72.1 | MAC |
| Av | (SEQ ID NO:6) | 73.5 | avium |
| P1.21c | (SEQ ID NO:7) | 73.5 | MAC |
| P1.3c | (SEQ ID NO:10) | 72.1 | MAC |
| MAC | (SEQ ID NO:8) | 73.5 | MAC |

FIG. 3 illustrates the sequences of five 25 nt MSqv probes within the 16s to 23s rRNA intergenic region and target specificity of a given sequence. MSqv-Av is *M. avium*-specific while all the others are MAC-specific. The inability of MSqv-Av probe to identify MAC or *M. intracellulare* is due to a single C to G (or C to U) base change 10 nt upstream is sufficiently destabilized by altering the "C" in position 132 to any other base whereby the probe identifies only the *M. avium* species. This single base "C" in position 132 is key to the identification of the broad MAC panel and when this single base is changed from "C" to another base this 25 nt probe becomes *M. avium* specific.

TABLE 10

A Single Base Change in a 25-mer MAC-specific Probe
Alters Its Specificity to Exclusively *M. avium*

| Sequevar | Sample ID | 132  13"  138<br>C. . . CG<br>Msqv P1 21 c | 132  13"  138<br>G. . . CG<br>Msqv-Av | 132  13"  138<br>U. . . CG<br>Msqv-Uracil | 132  13"  138<br>C. . . GG<br>Msqv-MAC | 132  13"  138<br>C. . . GA<br>Msqv P1 3c |
|---|---|---|---|---|---|---|
| Mav-A | TMC 1463 | 7 | 6 | 6.5 | 6 | 6 |
| Mav-B | SJB 2 | 6 | 5.5 | 6 | 5 | 6 |
| Min-A | 157 Manten | 5.5 | 0.25 | 0.25 | 6 | 7 |
| MAC-E | P49 | 5 | 0.25 | 0.25 | 5 | 6 |
| Min-A | P-42 | 6.5 | 0 | 0 | 6.5 | 7.5 |
| Min-A | 6845 | 5.5 | 0.25 | 0 | 6 | 7 |
| Min-A | ATCC 25122 | 5 | 0.25 | 0.25 | 6 | 6 |
| Min-A | Edgar Boone | 6 | 0.5 | 0.5 | 6 | 7 |
| Min-A | TMC 1473 | 6.5 | 0.25 | 0.5 | 6 | 7 |
| Min-A | Yandel | 7 | 0.25 | 0.25 | 6.5 | 7 |
| Min-A | P-54 | 5.5 | 0.25 | 0.5 | 6 | 6.5 |
| MAC-D | Melnick | 5 | 0.5 | 0.5 | 6 | 6.5 |
| na | Darden | 6.5 | 0.5 | 0.5 | 6 | 7 |
| MAC-A | W552 | 5 | 0 | 0 | 5.5 | 6 |
| Min-A | TMC 1419 | 5 | 2.25 | 2.25 | 6 | 6.5 |
| na | AT 545 Findley | 4.5 | 0.5 | 0.5 | 6 | 6.5 |
| Mav-B | 2993 | 6.5 | 6 | 5.5 | 5 | 6 |
| MAC-F | 5154 O'Connor | 6 | 0 | 0.25 | 5.5 | 7.5 |
| MAC-C | 23393 | 5.5 | 0.25 | 0.5 | 6 | 7.5 |
| na | CDC 1217 | 6 | 0.5 | 0.5 | 5.5 | 6 |
| MAC-B | 12645 | 5.5 | 0 | 0 | 6 | 6 |
| na | CDC 1195 | 5.5 | 0.25 | 0.5 | 6 | 6.5 |
| Min-A | 72-888 | 6.5 | 0 | 0 | 6.5 | 7.5 |
| Min-A | Hilberry 1244 | 6 | 0.25 | 0.5 | 6 | 7 |

Table 10 illustrates the significant change that the single base (at residue 132) change made in probe specificity. PCR amplification and detection were performed as previously mentioned using the MSqv F4/R5 primer set and the IPC primer set. The Mac Sequevar probe identifications are shown as column headings. The corresponding key base positions are shown and labeled according to Frothingham Mav-A sequevar alignment (Frothingham, J. Infect. Diseases, 169:308 (1994). The resulting amplified product from organisms in the panel was detected using the various probe-specific bead spots as shown in Table 10. IPC signal was positive in all cases (not shown). Sequevars Mav-A and Mav-B were used as *M. avium* controls, while all other organisms in the panel were MAC (species other than *M. avium*). Single or dual base variations at residues 137 and 138 did not alter the probe specificity from identifying a broad panel of MAC organisms (including *M. avium*). Frothingham et al., supra demonstrated that it was at residues 137 through 139 where there was variation between Mav sequevars and MAC (or Min) sequevars, but did not identify variations between *M. avium* and other species at residue 132.

The single residue as shown above each column is found in position 132, and the doublet residues shown are found (from left to right) in positions 137 and 138 of *M. avium* (Mav-A) sequevar as illustrated in Frothingham et al., supra. Although IPC results are not shown, a positive IPC signal in all cases was observed.

A probe was designed that concentrated on residue 132. When using a 25 nt probe where "C" is placed at residue 132 and "CG" are placed at residues 137 and 138, respectively (as in probe MSqv P1.21c), the probe retains the ability to hybridize with a broad spectrum of *M. avium*, *M. intracellulare,* and non-*M. avium,* non-*M. intracellular* MAC organisms within the panel tested. However, when residue 132 is changed to a "G" or to a "U" while maintaining the same "CG" configuration at residues 137 and 138 (as in probe MSqv-Av or Msqv-uracil, respectively), the probe only hybridizes with *M. avium* organisms, and is unable to hybridize with other organisms within the MAC. When using these 25 nt MAC-specific probes (P1.21c, P1.3c, MAC) it is important to have the base "C" at position 132. When this single base is changed to another base (as shown with P1.21c's conversion to MAC-Av or MAC-uracil), the 25 nt probe becomes *M. avium*-specific. Thus, the MSqv-Av probe can be used to distinguish *M. avium* organisms from other organism of the MAC.

There are several advantages to amplifying a small (88nt-100nt) product and using a small probe to identify organisms at the species level. These advantages include that the PCR process can be used to more efficiently amplify smaller (approx. 80–100nt) targets than larger targets. In addition, smaller targets are less prone to fragmentation by harsh sample preparation procedures than larger targets. Therefore if the target is small, there is a greater opportunity to amplify the entire gene region of interest.

There are also several methods of identifying organisms at the species level. One method involves amplifying a large portion of the genome that contains sufficient variability and designing species-specific probes. Typically, a single, large gene region is amplified using a single primer set, and multiple (species-specific) probes would be used to identify species-specific product. (See, for example, WO96/00298). Another method involves identifying a gene region that contains sufficient variability and designing multiple species-specific primer sets and species-specific probes (within this gene region) that can be used in a multiplexed assay. (See, for example, WO 96/00298). Other methods include identifying multiple gene regions that can be used to design species-specific primers and probes that, when used in combination, comprise a multiplexed assay that identify organisms at the species level. An example of this is described hereinabove (e.g. rpsl gene used to identify *M. intracellulare,* and Mav 19k gene used to identify *M. avium*).

There are advantages to using a single primer set when identifying organisms at the species level. When multiple primer sets are used in a multiplexed system to amplify targets, the potential for primer-primer interaction increases in direct proportion to the number of primers used. Primer-primer interaction may result in a decrease in assay sensitivity due to side product formation. Potential primer-primer interaction is minimized by using a single (Msqv) primer set and two specific probes each to either identify MAC or *M. avium*. With the present invention, an additional primer set (and corresponding probe) can be introduced into the multiplexed system (to identify *M. avium, M. intracellulare,* and the broad MAC) with minimal risk of primer interaction as only two target-specific primers would be required to identify three categories of MAC organisms at the species level.

While the foregoing invention has been described in some detail for purposes of clarity and understanding, it will be clear to one skilled in the art from a reading of this disclosure that various changes in form and detail can be made without departing from the true scope of the invention.

What is claimed:

1. An oligonucleotide probe for detecting *Mycobacterium avium*, said probe comprising nucleotide sequence SEQ ID NO:1: 5' CCC TGA GAC AAC ACT DGG TCC GTC C 3', wherein D is any nucleotide other than C.

2. The oligonucleotide probe according to claim 1 wherein D is G or U.

3. The oligonucleotide probe according to claim 1 wherein D is G.

4. A kit comprising:
   (i) one or more primers consisting of sequences selected from the group consisting of SEQ ID NO:2, SEQ ID NO:3, SEQ ID NO:4, SEQ ID NO:5, SEQ ID NO:6, SEQ ID NO:7, SEQ ID NO: 8, SEQ ID NO:9, SEQ ID NO:10;
   (ii) one or more primers consisting of sequences selected from the group consisting of SEQ ID NO:11, SEQ ID NO:12, SEQ ID NO:13; and
   (iii) one or more primers consisting of sequences selected from the group consisting of SEQ ID NO:14, SEQ ID NO:15, SEQ ID NO:16.

5. A composition comprising:
   i) one or more oligonucleotides consisting of sequences selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 and one or more oligonucleotides consisting of sequences selected from the group consisting of SEQ ID NO:11, SEQ ID NO:12, SEQ ID NO:13, or
   ii) one or more oligonucleotides consisting of sequences selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 and one or more oligonucleotides consisting of sequences selected from the group consisting of SEQ ID NO:14, SEQ ID NO:15, SEQ ID NO:16, or
   iii) one or more oligonucleotides consisting of sequences selected from the group consisting of SEQ ID NO:11, SEQ ID NO:12, SEQ ID NO:13 and one or more oligonucleotides consisting of sequences selected from the group consisting of SEQ ID NO:14, SEQ ID NO:15, SEQ ID NO:16, or
   iv) one or more oligonucleotides consisting of sequences selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 and one or more oligonucleotides consisting of sequences selected from the group consisting of SEQ ID NO:11, SEQ ID NO:12, SEQ ID NO:13 and one or more oligonucleotides consisting of sequences selected from the group consisting of SEQ ID NO:14, SEQ ID NO:15, SEQ ID NO:16.

* * * * *